United States Patent [19]
Asmussen et al.

[11] Patent Number: 6,156,764
[45] Date of Patent: Dec. 5, 2000

[54] MORPHINE AND DIAMORPHINE SALTS OF ANIONIC NON-NARCOTIC ANALGESICS OF THE SUBSTITUTED CARBOXYLIC ACID TYPE

[75] Inventors: Bodo Asmussen, Bendorf-Sayn; Walter Müller, Neuwied; Walter Riess, Ansbach, all of Germany

[73] Assignee: LTS Lohmann Therapie-Systeme GmbH, Germany

[21] Appl. No.: 09/137,078

[22] PCT Filed: Feb. 15, 1997

[86] PCT No.: PCT/EP97/00711

§ 371 Date: Oct. 28, 1999

§ 102(e) Date: Oct. 28, 1999

[87] PCT Pub. No.: WO97/31918

PCT Pub. Date: Sep. 4, 1997

[30] Foreign Application Priority Data

Feb. 28, 1996 [DE] Germany ............ 196 07 395

[51] Int. Cl.$^7$ ...................................... A01N 43/42
[52] U.S. Cl. .................. 514/282; 546/44; 546/46
[58] Field of Search ................. 514/282; 546/44, 546/46

[56] References Cited

U.S. PATENT DOCUMENTS 4,404,209   9/1983   Schmidt ................... 424/260

FOREIGN PATENT DOCUMENTS

| 137600 | 7/1984 | European Pat. Off. ............ 514/285 |
| 472501 | 8/1991 | European Pat. Off. ............ 514/285 |
| 649657 | 4/1995 | European Pat. Off. ............ 514/285 |
| 95/04058 | 8/1991 | WIPO ................................ 514/285 |

*Primary Examiner*—James H. Reamer
*Attorney, Agent, or Firm*—James E. Klaniecki; Ann W. Speckman

[57] ABSTRACT

The present invention relates to morphine and diamorphine salts of anionic non-narcotic analgesics belonging to the type of substituted carboxylic acids, preferably the morphine and diamorphine salts of diclofenac (Formula 1); to processes for their production, the use of these salts in the treatment of diseases, as well as to pharmaceutical preparations comprising these salts.

25 Claims, No Drawings

MORPHINE AND DIAMORPHINE SALTS OF ANIONIC NON-NARCOTIC ANALGESICS OF THE SUBSTITUTED CARBOXYLIC ACID TYPE

TECHNICAL FIELD OF THE INVENTION

The present invention relates to morphine and diamorphine salts of anionic non-narcotic analgesics belonging to the type of substituted carboxylic acids, preferably the morphine and diamorphine salts of diclofenac (Formula 1). The present invention further relates to processes for their production, the use of these salts in the treatment of diseases, as well as to pharmaceutical preparations comprising these salts.

BACKGROUND OF THE INVENTION

Pain is one of the most frequent signs of a disease or a damage. Though pain is to be understood as a warning and protective function of the organism, patients concerned generally call for pain-killing or at least pain-relieving substances. For this reason, one of the most important concerns in medicine is to provide such substances. The function of these substances, so-called analgesics, is to reduce or suppress the sensation of pain when given in therapeutic doses without having a general narcotic effect in these doses. Based on their potency, therapeutic mechanism and side effects one distinguishes between two groups of analgesics: very potent analgesics acting on the central nervous system and low to moderately potent ones primarily having a peripheral action. Active substances acting on the central nervous system frequently involve a habit-forming potential which might develop into addiction. Morphine (Formula 3a) is one example of an active substance acting on the central nervous system and having such a risk. In the form of its inorganic salts, for example its hydrochloride or sulfate, morphine is commercially available for parenteral or peroral application to control acute posttraumatic or postoperative pain, as well as chronic pain, for example, in the state of advanced cancer.

A derivative of morphine, diacetylmorphine (Formula 3b), also known as diamorphine or heroin, is dealt and consumed among drug addicts without any pharmacological, pharmaceutical, or pharmacokinetic control. Its qualified use in the treatment of drug addiction is a scientific and sociological problem that has not yet been solved.

In order to reduce the risk of morphine dependence in the clinical use of morphine preparations, other analgesics, preferably non-narcotic peripheral preparations, are administered at the same time or alternately. Owing to the great variety of peripherally effective analgesics, their different potency and thus their different dosage, there is a great uncertainty concerning the choice of preparations to be combined, resulting in patient discomfort because of the amount of drugs to be taken.

SUMMARY OF THE INVENTION

It is the object of the present invention to provide new analgesics having a maximum analgesic effect with minimum side effects.

This object is achieved by the new active substances characterized in the claims and by the pharmaceutical preparations comprising these active substances.

The active substances according to the present invention are the morphine and diamorphine salts of anionic non-narcotic analgesics of the type substituted carboxylic acids. Suitable anionic non-narcotic analgesics belonging to the type of substituted carboxylic acids include: diclofenac, indomethacin, sulindac, ketoprofen, or fenbufen.

The present invention preferably includes the salts morphine-diclofenate (Formula 1a) and diamorphine-diclofenate (Formula 1b) consisting of the anionic peripheral analgesic diclofenac ([2-[(2,6-dichlorophenyl)-amino]-phenyl]-acetic acid (Formula 2)) and the cationic analgesic morphine (Formula 3a) acting on the central nervous system or its derivative diacetylmorphine (Formula 3b), also referred to as diamorphine. In Formula 1, R may represent H or $CH_3CO$. If R stands for H, it is morphine-diclofenate (Formula 1a); if R stands for $CH_3CO$, it is diamorphine-diclofenate (Formula 1b).

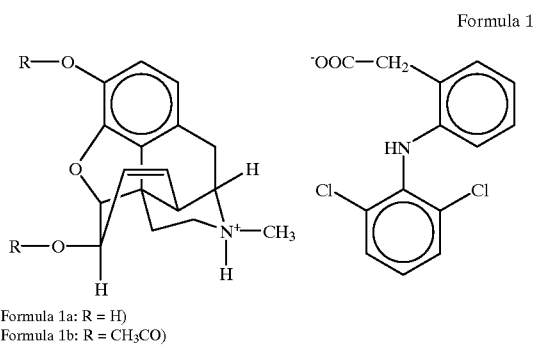

(Formula 1a: R = H)
(Formula 1b: R = $CH_3CO$)

Formula 1

The above-mentioned non-narcotic analgesics of the type substituted carboxylic acids and their salts are known. The sodium, potassium, diethylammonium salts of diclofenac (Formula 2) ([2-[2,6-dichlorophenyl)-amino]-phenyl]-acetic acid) are used, for example, in the treatment of painful inflammatory processes. Preparations for the oral, rectal, parenteral, or topical application have been on the market for some time.

Diclofenac (Formula 2) has proved to be the most potent non-steroid anti-inflammatory agent/analgesic owing to the effective dose and total clearance.

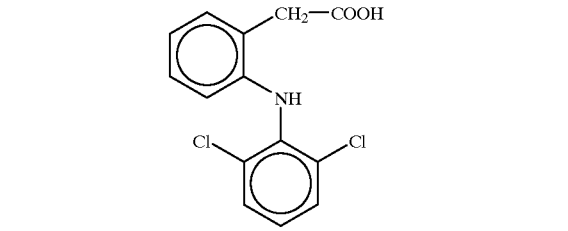

Formula 2

When applied perorally, diclofenac (Formula 2) is clinically pharmacologically effective in the dosage range of 0.08 to 0.16 mmol/8 hrs., and it is therefore in the range of the molar dosage of morphine (Formula 3a). For comparison: Morphine is effective in the dosage range of 0.035 to 0.35 mmol/6 hrs.

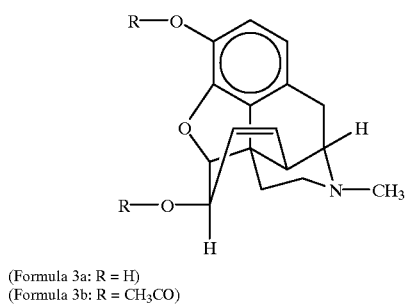

Formula 3

(Formula 3a: R = H)
(Formula 3b: R = CH₃CO)

In Formula 3 R may be H (morphine) or CH₃CO (diamorphine)

The salts according to the present invention which are composed of the base of the narcotic analgesic of Formula 3, wherein R stands for H or CH₃CO, and the acid of the non-narcotic analgesic of the type substituted carboxylic acids, preferably morphine or diamorphine-diclofenate (Formula 1a or 1b), make it advantageously possible to use the individual components in a smaller dose as compared with preparations of single-entity drugs in the form of their inorganic salts in free combination with conventional commercial administration forms.

The salts according to the present invention, preferably morphine or diamorphine-diclofenate (Formula 1a or 1b), may be used instead of classical morphine preparations to alleviate pain, but with less side effects. In the case of the diclofenates according to the present invention, the gastrointestinal tolerance limits of diclofenac (Formula 2) represent a safeguard for observing the officially recommended dose. For that reason, potential drug abuse inherent in the availability of morphine preparations is rendered more difficult by the morphine or diamorphine salts according to the present invention. The morphine or diamorphine salts according to the present invention enable the physician to include the patient in a scheme of treatment, since less drugs can be combined freely and less unprofessional variations of the medical recommendation are possible.

The diamorphine salts according to the present invention make it possible for the first time to include diamorphine in a therapy.

The topical preparations of the salts according to the present invention, in particular those of morphine-diclofenate (Formula 1a) and diamorphine-diclofenate (Formula 1b), allow minimum active substance supply with reduced systemic side effects, for example, during the withdrawal phase in addiction therapy.

DETAILED DESCRIPTION

The active substances according to the present invention are produced from acid or base components known per se. It is preferable to react non-narcotic analgesics of the type substituted carboxylic acids, in particular [2-[(2,6-dichlorophenyl)-amino]-phenyl]-acetic acid of Formula 2 or a base salt thereof, with preferably at least the equimolar amount of morphine (Formula 3a) or the morphine derivative according to Formula 3b or a suitable salt thereof. Suitable salts of non-narcotic analgesics of the type substituted carboxylic acids particularly include salts of bases which can easily be removed from the reaction mixture. These include, for example, bases which are more volatile or weaker than morphine or diamorphine (Formula 3a or 3b), or those forming soluble salts with the anionic non-narcotic analgesic of the type substituted carboxylic acids, in particular [2-[(2,6-dichlorophenyl)-amino]-phenyl]-acetic acid of Formula 2, more readily than the salts according to the present invention do. These salts are other organic ammonium salts, for example. Metallic salts which, during the reaction with a suitable acid salt of morphine or diamorphine (Formula 3a or 3b), form poorly soluble salts of this acid can also be used as salts, for example, calcium salts.

Salts of morphine or diamorphine (Formula 3a or 3b) suitable to be used in the process include, for example, salts with acids which may be eliminated from the reaction mixture, e.g., salts of volatile acids. It is also possible to use acids which are weaker than the non-narcotic analgesic of the type substituted carboxylic acids, or which form poorly soluble salts with metal cations, for example $Ca^{2+}$. Salts of morphine or diamorphine (Formula 3a or 3b) include, for example, salts of the compounds according to Formula 3a or 3b with inorganic acids, e.g., hydrochlorides, sulfates, or phosphates, or salts of morphine or diamorphine (Formula 3a or 3b) and organic acids, e.g., fumarates, maleates, or oxalates.

It is preferable to carry out the reaction of the non-narcotic analgesics of the type substituted carboxylic acids, preferably [2-[(2,6-dichlorophenyl)-amino]-phenyl]-acetic acid (Formula 2), with a base of Formula 3 in an inert solvent. If necessary, the reaction may be carried out under cooling or heating, for example, in a temperature range of about 0 to about 100° C., preferably at room temperature. Reaction may be conducted in a closed vessel and/or under inert gas atmosphere, e.g., in nitrogen atmosphere.

Suitable inert solvents include, for example, alcohols, ethers, ketones, carboxylic acid esters, amides, sulfoxides, chlorinated hydrocarbons, or mixtures of these solvents. Low alkanols may be used as alcohols, preferably methanol or ethanol; di-low-alkyl ethers, preferably diethyl ethers, cyclic ethers, preferably dioxan or tetrahydrofuran may be used as ethers; di-low-alkyl ketones, preferably acetone may be used as ketones; low-alkyl carboxylic acid esters, preferably acetic acid ethyl ester may be used as carboxylic acid esters; N,N-di-low-alkyl amides, preferably N,N-dimethylformamide may be used as amides; di-low-alkyl sulfoxides, preferably dimethyl sulfoxide may be used as sulfoxides; and methylene chloride or chloroform may be used as chlorinated hydrocarbons.

Non-narcotic analgesics of the type substituted carboxylic acids, in particular [2-[(2,6-dichlorophenyl)-amino]-phenyl]-acetic acid (Formula 2), may also be formed under the reaction conditions from the corresponding esters, preferably low-alkyl esters, by hydrolysis in the presence of a base, for example, NaOH. Morphine or diamorphine of Formula 3a or 3b may also be released under the reaction conditions from the acid salts, preferably from hydrochlorides, sulfates, or phosphates, in the presence of stoichiometric amounts of suitable bases, for example, NaOH.

According to a preferred embodiment of the process, the non-narcotic analgesic of the type substituted carboxylic acids is directly reacted as a free acid according to formula 2 with morphine or diamorphine of Formula 3a or 3b in the form of a base in a suitable solvent. The present invention also relates to those production processes wherein the starting materials are manufactured in situ or wherein a starting material is obtained under the reaction conditions from a derivative and/or is used in the form of a mixture, e.g., in the case of morphine or diamorphine (Formula 3a or 3b) as a raw alkaloid mixture. The present invention also includes processes wherein liquid or solid charged or uncharged inorganic or organic adsorbents are used. For example, ion exchangers may be used to bind the cationic or anionic component of the salts according to the present invention which are subsequently reacted with the complementary anionic or cationic component. It is also possible to use uncharged inorganic or organic adsorbents to prepare or purify the salts according to the present invention.

Moreover, the present invention relates to pharmaceutical preparations which, in addition to pharmaceutical adjuvants known per se, comprise the salts of morphine (Formula 3a) or diacetylmorephine (Formula 3b) and analgetically effective carboxylic acids, in particular the salts of Formula 1a and 1b, morphine-diclofenate or diamorphine-diclofenate. The present invention also relates to methods for the production of these pharmaceutical preparations. The pharmaceutical preparations according to the present invention relate to preparations for enteral, e.g., oral or rectal administration; parenteral, e.g., intravenous, intramuscular, or subcutaneous application; or for topical application, which comprise the salts according to the present invention, in particular the salts of Formula 1a and 1b, either alone or together with pharmaceutically applicable carriers, in particular those suitable for controlled active substance release.

In standard dosage forms for peroral use the content of the active substance according to the present invention preferably ranges between of 10 and 90%. To produce tablets or coated tablet cores, the active substance is combined, for example, with solid powdery carriers, such as lactose, saccharose, sorbitol, mannitol, starches or amylopectin; cellulose derivatives, gelatin, or polyvinyl pyrrolidone, optionally by adding lubricants, such as magnesium or calcium stearate or polyethylene glycols; as well as with highly dispersed silicic acid. Cores of coated tablets are coated, for example, with concentrated sugar solutions which may optionally comprise additives, such as gum arabic, talc and/or titanium dioxide, or with a lacquer dissolved in highly volatile organic solvents or solvent mixtures. Dyes may be added to these coatings, for example, to mark different active substance doses. Further suitable oral forms of administration include hard capsules made of gelatin and soft closed capsules made of gelatin and a softener, such as glycerol. The first-mentioned preferably comprise the active substance as a granular material mixed with lubricants, such as talc or magnesium stearate, and optionally with stabilizers, such as sodium pyrosulfite ($Na_2S_2O_5$) or ascorbic acid. In soft capsules, the active substance according to the present invention is preferably dissolved or suspended in suitable liquids, such as liquid polyethylene glycols, wherein stabilizers may also be added. For controlled release, the active substances according to the present invention may be incorporated in a pharmaceutically acceptable carrier matrix, or be enclosed in a membrane-defined reservoir which activates in vivo for appropriate release kinetics.

Suppositories are suitable standard dosage forms for rectal use; these consist of the active substance salt according to the present invention within a base for suppositories which is based on natural or synthetic triglycerides having a suitable melting point, for example, cacao butter, or on polyethylene glycols or suitable higher fatty alcohols.

Solutions of the active substance according to the present invention are preferably suitable for parenteral administration. It is also possible to use suspensions thereof, such as adequate oily injection suspensions. In this case, suitable lipophilic solvents or vehicles, such as oils, e.g., sesame oil, or synthetic fatty acid esters, e.g., ethyl oleate or triglycerides, or aqueous injection suspensions comprising viscosity-increasing substances, e.g., sodium carboxymethylcellulose, sorbitol, and/or dextran, and optionally also stabilizers are used.

Topically applicable pharmaceutical preparations of the salts according to the present invention, preferably of morphine-diclofenate (Formula 1a) or diamorphine-diclofenate (Formula 1b), include creams, ointments, gels, pastes, foams, tinctures, and solutions comprising about 0.5 to about 20% active substance according to the present invention. A salt according to the present invention, preferably morphine-diclofenate (Formula 1a) or diamorphine-diclofenate (Formula 1b), may also be incorporated into patches or so-called transdermal therapeutic systems (TTS); from these the active substance components act on the skin over a defined area of the body surface in occlusive manner at a controlled release rate and are appropriately brought to transdermal absorption.

The following Examples are given for illustration purposes and are not intended to limit the present invention:

METHODS OF PRODUCING THE SALTS

EXAMPLE 1

An equimolar amount of an aqueous solution of diclofenac sodium salt is added to an aqueous solution of morphine hydrochloride, this is brought into solution by stirring and optional heating. The forming morphine diclofenate precipitate is sucked off and dried over a molecular sieve in a desiccator.

The content of both morphine and diclofenac can be detected in the crystalline substance by IR spectroscopy.

The melting point of the salts amounts to about 143° C. and is therefore clearly different from those of the starting materials (morphine hydrochloride: 255° C., diclofenac sodium salt: 280° C.)

EXAMPLE 2

Equimolar amounts of morphine base or diamorphine base and of [2-[(2,6-dichlorophenyl)-amino]-phenyl]-acetic acid are dissolved in ethanol, mixed in a round-bottom flask, and evaporated to dryness in a rotary evaporator. The evaporation residue is recrystallized from ethanol under addition of petroleum ether, sucked-off and vacuum-dried.

EXAMPLE 3

1 millimole of morphine hydrogen sulfate or diamorphine hydrogen sulfate is dissolved in water, made alkaline with an aqueous sodium bicarbonate solution, and extracted with acetic ester. Also, 1 millimole of diclofenac sodium is dissolved in water, acidified with dilute hydrochloric acid, and extracted with acetic ester. Both extracts are separately dried over anhydrous sodium sulfate. Subsequently, both extracts are joined, mixed, and evaporated to dryness in the round-bottom flask at the rotary evaporator. The evaporation residue is recrystallized from ethanol under addition of petroleum ether and vacuum-dried.

PROCESS OF PRODUCING A PHARMACEUTICAL PREPARATION

EXAMPLE 4

For peroral administration morphine-diclofenate or diamorphine-diclofenate is ground finely, and mixed homogeneously with powdery carrier substances, such as lactose, saccharose, sorbitol, mannitol, or starches, until four times the amount is achieved. Single doses, for example, 0.05 millimole of active substance equivalents, are weighed into gelatin capsules.

What is claimed is:

1. A salt of a cationic narcotic analgesic with an anionic non-narcotic acid characterized in that the base of the narcotic analgesic corresponds to the formula

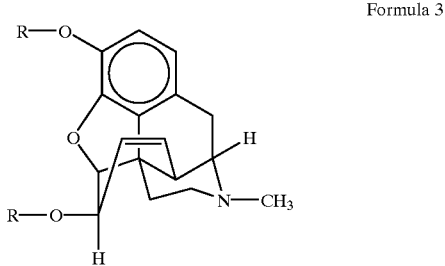

Formula 3 wherein R stands for H or $CH_3CO$, and the non-narcotic analgesic belongs to the type of substituted carboxylic acids.

2. The salt according to claim 1 characterized in that the anion of the non-narcotic analgesic of the type substituted carboxylic acids is diclofenac, indomethacin, sulindac, ketoprofen, or fenbufen, preferably is diclofenac.

3. A process for the production of the salt according to claim 1 or 2 characterized in that the base of the narcotic analgesic corresponds to formula 3, wherein R stands for H or $CH_3CO$ or a suitable salt thereof, and is reacted with the acid of the non-narcotic analgesic of the type substituted carboxylic acids or with a base salt thereof in an inert solvent at a temperature ranging from 0 to 100° C.

4. The process according to claim 3 characterized in that a salt of the non-narcotic analgesic of the type substituted carboxylic acids is used with bases which are more volatile or weaker than the base of the narcotic analgesic of formula 3, wherein R stands for H or $CH_3CO$, or that a salt of the non-narcotic analgesic of the type substituted carboxylic acids is used with bases which form salts with the non-narcotic analgesic of the type substituted carboxylic acids, which are more readily soluble than the salt according to claim 1.

5. The process according to claim 4 characterized in that an organic ammonium salt or a metallic salt, preferably a calcium salt, is used as salt.

6. The process according to any one of claims 3 to 5 characterized in that a salt from the base of the narcotic analgesic of formula 3, wherein R stands for H or $CH_3CO$, is used with acids which are more volatile or weaker than the acid of the non-narcotic analgesic of the type substituted carboxylic acids, or that a salt from the base of the narcotic analgesic of formula 3, wherein R stands for H or $CH_3CO$, is used with acids which form poorly soluble salts with metal cations, preferably with $Ca^{2+}$.

7. The process according to claim 6 characterized in that a salt from the base of the narcotic analgesic of formula 3, wherein R stands for H or $CH_3CO$, is used with inorganic acids, preferably a hydrochloride, sulfate, or phosphate, or that a salt from the base of the narcotic analgesic of formula 3, wherein R stands for H or $CH_3CO$, is used with organic acids, preferably a fumarate, maleate, or oxalate.

8. The process according to any one of claims 3 to 5 characterized in that diclofenac ([2-[(2,6-dichlorophenyl)-amino]-phenyl]-acetic acid) is used as the acid of the non-narcotic analgesic of the type substituted carboxylic acids.

9. A process for the production of a salt according to claim 1 or 2 characterized in that an acid salt of the basic narcotic analgesic of formula 3, wherein R stands for H or $CH_3CO$, preferably the hydrochloride, sulfate, or phosphate, is reacted with an ester of the non-narcotic analgesic of the type substituted carboxylic acids, preferably a low-alkyl ester, in the presence of a base, preferably NaOH, in an inert solvent at a temperature ranging from 0 to 100° C.

10. A process for the production of the salt according to claim 1 or 2 characterized in that the base of the narcotic analgesic of formula 3, wherein R stands for H or $CH_3CO$, is reacted with the acid of the non-narcotic analgesic of the type substituted carboxylic acids in an inert solvent at a temperature ranging from 0 to 100° C.

11. The process according to any one of claims 9 or 10 characterized in that the base of the narcotic analgesic of formula 3, wherein R stands for H or $CH_3CO$, is used as raw alkaloid extract in admixture.

12. A process for the production of the salt according to claim 1 or 2 characterized in that the cation or the base of the narcotic analgesic of formula 3, wherein R stands for H or $CH_3CO$, or the anion or the acid of the non-narcotic analgesic of the type substituted carboxylic acids is bound to liquid or solid charged or un-charged inorganic or organic adsorbents, preferably ion exchangers, and is reacted with the respective complementary anionic or cationic component in an inert solvent at a temperature ranging form 0 to 100° C.

13. The process according to any one of claims 3, 4, 5, 9, 10 and 12 characterized in that at least equimolar amounts of reactants are used.

14. The process according to any one of claims 3, 4, 5, 9, 10 and 12 characterized in that the reaction is carried out at room temperature and/or under inert gas atmosphere, preferably under nitrogen atmosphere.

15. The process according to any one of claims 3, 4, 5, 9, 10 and 12 characterized in that alcohols, ethers, ketones, carboxylic acid esters, amides, sulfoxides, chlorinated hydrocarbons, or mixtures of these solvents are used as inert solvents.

16. The process according to claim 15 characterized in that low alkanols, preferably methanol or ethanol are used as alcohols; di-low-alkyl ethers or cyclic ethers, preferably diethyl ether, dioxan or tetrahydrofuran are used as ethers; di-low-alkyl ketones, preferably acetone are used as ketones; low-alkyl carboxylic acid esters, preferably acetic acid ethyl ester are used as carboxylic acid esters; N,N-di-low-alkyl amides, preferably N,N-dimethyl formamide are used as amides; di-low-alkyl sulfoxides, preferably dimethyl sulfoxide are used as sulfoxides; and methylene chloride or chloroform are preferably used as chlorinated hydrocarbons.

17. A pharmaceutical preparation characterized in that it comprises a salt according to claim 1 or 2 in addition to pharmaceutical adjuvants known per se.

18. The pharmaceutical preparation according to claim 17 for enteral, for example, oral or rectal administration, or for parenteral, for example, intravenous, intramuscular, subcutaneous, or topical application.

19. The use of the salt according to claim 1 or 2 in galenic forms of preparation or for their production.

20. The salt according to claim 1 or 2 for the therapeutic treatment of human and animal organisms.

21. The salt according to claim 1 or 2 for the therapeutic treatment of pain.

22. The pharmaceutical preparation according to claim 17 or 18 for the therapeutic treatment of human and animal organisms.

23. The pharmaceutical preparation according to claim 17 or 18 for the therapeutic treatment of pain.

24. A process for the therapeutic treatment of human or animal organisms characterized in that a salt according to any one of claims 1 or 2 or a pharmaceutical preparation according to any one of claims 17 or 18 is used.

25. A process for the treatment of pain characterized in that a salt according to any one of claims 1 or 2 or a pharmaceutical preparation according to any one of claims 17 or 18 is used.

* * * * *